(12) United States Patent
Yamamoto et al.

(10) Patent No.: US 10,220,998 B2
(45) Date of Patent: Mar. 5, 2019

(54) RECLOSABLE PACKAGE AND A METHOD OF MAKING THE SAME

(71) Applicant: The Procter & Gamble Company, Cincinnati, OH (US)

(72) Inventors: Yoichiro Yamamoto, Cologne (DE); Jan Michael Trinkaus, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/795,394

(22) Filed: Oct. 27, 2017

(65) Prior Publication Data
US 2018/0118438 A1  May 3, 2018

(30) Foreign Application Priority Data

Oct. 28, 2016 (EP) ..................................... 16196155

(51) Int. Cl.
*A47K 10/42* (2006.01)
*B65B 11/48* (2006.01)
(Continued)

(52) U.S. Cl.
CPC ...... *B65D 75/5827* (2013.01); *A61F 13/5511* (2013.01); *A61F 13/55145* (2013.01);
(Continued)

(58) Field of Classification Search
CPC .... B65D 75/5827; B65D 75/58; B65D 75/52; B65D 85/07; B65D 85/62; B65D 71/063;
(Continued)

(56) References Cited

U.S. PATENT DOCUMENTS 3,259,303 A * 7/1966 Repko ................ B65D 75/5833
206/497
3,349,993 A * 10/1967 Ells ...................... B65D 75/585
383/203
(Continued)

FOREIGN PATENT DOCUMENTS

DE  3914595 A1  11/1990

OTHER PUBLICATIONS

CM4635Q PCT International Search Report dated Jan. 22, 2018 (13 pages).
EP International Search Report dated Mar. 2, 2017 (7 pages).

*Primary Examiner* — Steven A. Reynolds
*Assistant Examiner* — Javier A Pagan
(74) *Attorney, Agent, or Firm* — Andrew J. Hagerty

(57) ABSTRACT

A flexible reclosable package contains disposable and compressed consumer products. The package has a hexahedral shape with a top panel, a bottom panel, a front panel, a back panel, a left side panel and a right side panel. A hooded portion defines the top panel, a portion of the front panel, a portion of the first right side panel portion and a portion of the first left side panel portion. A pleated portion is provided adjacent to the hooded portion and extends from a first side panel seam to a second side panel seam. A first line of weakness, which is not visible from the exterior of the package when the package closed, is provided in the pleated portion. The flexible reclosable package can be converted from a closed configuration to an open configuration upon opening the package along the line of weakness.

11 Claims, 8 Drawing Sheets

(51) Int. Cl.
  *B65D 75/58* (2006.01)
  *A61F 13/551* (2006.01)
  *B65B 61/06* (2006.01)
  *B65B 61/18* (2006.01)
  *B65D 71/06* (2006.01)
  *B65D 85/62* (2006.01)
  *B65D 85/07* (2017.01)

(52) U.S. Cl.
  CPC ........ *A61F 13/55175* (2013.01); *B65B 11/48* (2013.01); *B65B 61/06* (2013.01); *B65B 61/18* (2013.01); *B65D 71/063* (2013.01); *B65D 85/07* (2018.01); *B65D 85/62* (2013.01); *A47K 10/42* (2013.01); *B65D 2571/00592* (2013.01); *B65D 2571/00672* (2013.01); *B65D 2575/586* (2013.01)

(58) Field of Classification Search
  CPC ................ B65D 71/06; A61F 13/5511; A61F 13/55105; A61F 13/551; A61F 13/55145; A61F 13/55175; B65B 11/48; B65B 61/06; B65B 61/18
  USPC .......................................... 206/494, 812, 233
  See application file for complete search history.

(56) References Cited

U.S. PATENT DOCUMENTS

| | | |
|---|---|---|
| 2007/0219521 A1 | 9/2007 | Hird et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |
| 2014/0348445 A1 | 11/2014 | Siesto Casanova et al. |

\* cited by examiner

Fig. 3A
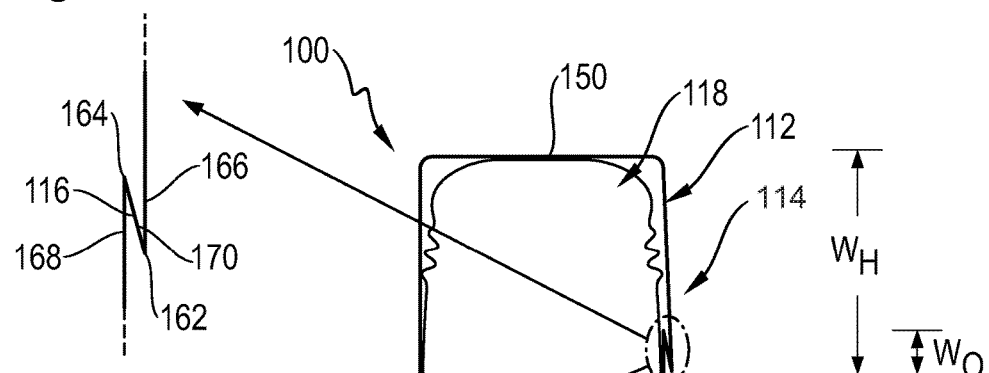
Fig. 3B
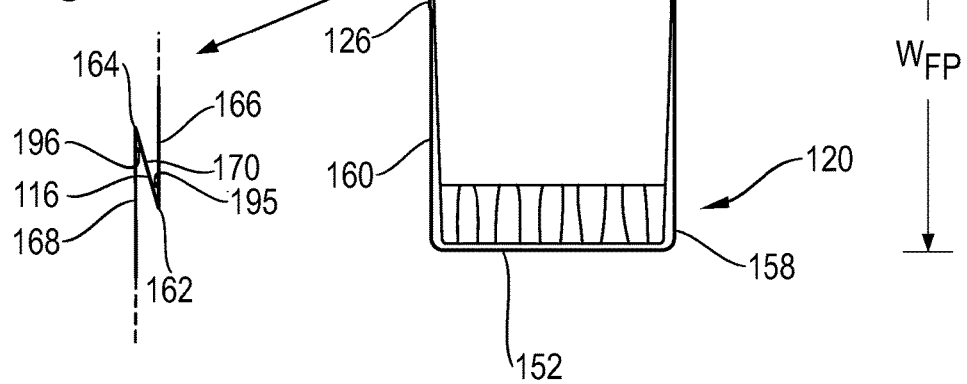
Fig. 3

RECLOSABLE PACKAGE AND A METHOD OF MAKING THE SAME

FIELD

The present disclosure relates to packages and methods of making packages, and more particularly, to sealed reclosable packages and a method of making the same.

BACKGROUND

The field of disposable absorbent articles includes a wide variety of consumer products, including diapers, bibs, wipes, sanitary napkins, tampons, etc. In some cases, the absorbent articles are packaged in a flexible package, such as a package made of film.

Flexible packages for containing absorbent articles may include opposing first and second panels. Each panel may define a top edge portion, a bottom edge portion, a left side edge portion, and a right side edge portion. The first and second panels may be joined at a first seam along left side edge portions of the first and second panels and at a second seam along right side edge portions of the first and second panels. The primary package may include a reclosable feature along a top or bottom edge portion of the package for opening and closing the packages. In some primary packages, the reclosable features may include a lid, tape tab fastener, hook and loop fastener, snap, button, or latch, for example. However, adding reclosable features to the flexible package may add cost and complexity to the manufacturing of the package.

Some flexible packages include an integrated reclosable feature, such as a hood, in the second panel of the primary package. The hood may be positioned proximate to the top or bottom edge portion of the primary package. The hood may be configured in a closed configuration and an open configuration. In the closed configuration, the hood may cover the absorbent articles contained therein. In the open configuration, the hood may be folded away from the first panel to create an opening in the package that exposes the absorbent articles contained therein. However, the first and second panels may be integrally connected in the portion of the panels opposite the hood. As such, the hood may provide the only access to the flexible package for inserting absorbent articles during the packaging process, and for removing the absorbent articles from the flexible package at the time of use by the consumer. Without using additional refastenable features, the package may not be sealed at the time of purchasing the flexible package of absorbent articles because of the opening created by the hood. Consequently, the absorbent articles may be subject to tampering or contamination before the package of absorbent articles is purchased by the consumer.

A flexible package provided with a hood is for example described in WO 2014/190102A1.

It would be beneficial to provide a reclosable flexible package which can be opened and reclosed easily and conveniently also when the package is tightly filled with compressed absorbent articles. Moreover, the flexible package should have aesthetic appearance, both when the package is in the open and closed configuration. It would also be desirable to protect the package from pre-mature opening.

SUMMARY

The flexible reclosable package is integrally formed from a single piece of material. The package contains disposable and compressed consumer products, such as absorbent articles. It has a hexahedral shape with a top panel, a bottom panel, a front panel, a back panel, a left side panel and a right side panel.

The right side panel comprises a first right side panel portion adjacent to the front panel and a second right side panel portion adjacent to the back panel. The first and second right side panel portions are joined to each other along first side panel seam.

The left side panel comprises a first left side panel portion adjacent to the front panel (158) and a second left side panel portion adjacent to the back panel. The first and second left side panel portions being joined to each other along a second side panel seam.

The package has a longitudinal dimension extending from the first side panel seam to the second side panel seam. A third seam joins extends along the longitudinal dimension of the package. The third seam may extend through the back panel, through the bottom panel, through the top panel or, though less desirable, through the front panel.

A hooded portion defines the top panel, a portion of the front panel, a portion of the first right side panel portion and a portion of the first left side panel portion.

A pleated portion is provided adjacent to the hooded portion and extends along the longitudinal dimension of the package from the first side panel seam to the second side panel seam through the first right side panel portion, the front panel, and the first left side panel portion, wherein a first line of weakness is provided in the pleated portion.

The flexible reclosable package can be converted from a closed configuration to an open configuration upon opening the package along the line of weakness. The first line of weakness is not visible from the exterior of the package when the package is in the closed configuration.

The flexible reclosable package may be sealed prior to opening the package at the line of weakness.

The invention further relates to a method of forming a flexible reclosable package, the method comprising the steps of:

a. Advancing a continuous length of material in a machine direction, wherein the continuous length of material has a first side and a second side and defines a first edge region with a first side edge and a second edge region with a second side edge separated in a cross-machine direction by a central region.

b. Forming a line of weakness along the machine direction of the central region of the continuous length of material.

c. Folding the continuous length of material along the machine direction to form a continuous pleat, wherein the continuous pleat comprises first and second continuous folds that form first, second, and third overlapping continuous pleated portions. The third continuous pleated portion is positioned between the first continuous pleated portion and the second continuous pleated portion. The line of weakness is provided in the continuous pleat, wherein the first and second continuous folds extend in the machine direction. The line of weakness may be provided in the third continuous pleated portion, in the second fold, or in the second continuous pleated portion.

d. Advancing a plurality of consumer products, such as disposable absorbent articles, along machine direction wherein the plurality of consumer products are arranged in a group, the group having, along machine direction, a leading edge and a trailing edge.

e. Folding the continuous length of material around the plurality of consumer products arranged in a group.

f. Joining the first and second side edges of the continuous length of material to each other to form a third seam along machine direction.

g. Sealing the continuous length of material along cross-machine direction adjacent to the leading edge and the trailing edge of the plurality of consumer products arranged in a group, thereby forming the first and second side panel seams of the flexible reclosable package and forming a closed package around the plurality of consumer products arranged in a group.

h. Cutting the continuous length of material in the cross-machine direction in or adjacent to the first and second side panel seams to form a flexible reclosable package. The flexible reclosable package has a front panel, a back panel, a bottom panel, a top panel and left and right side panels. The central region of the continuous length of material may form the front panel, the first right side panel portion and the first left side panel portion of the package.

The third seam may be formed in the back panel of the present invention. Alternatively, it is also possible to form the third seam in the bottom panel, in the bottom panel, or, though less desirable, even in the front panel. Typically, the third seam will be formed in the back panel.

The method of folding a continuous length of material around one or more products, wherein the continuous length of material and the one or more products are advancing in machine direction while the continuous length of material is folded around the products, is generally a type of process which is often referred to as "flow wrap" process to form a packaging. Flow wrapping packaging processes are generally well known in the art.

BRIEF DESCRIPTION OF THE DRAWINGS

FIG. 3 is a sectional view of the sealed, reclosable package of FIG. 1 taken along lines 3-3.

FIG. 3A is an enlarged view on the pleated portion of FIG. 3.

FIG. 3B is an enlarged view on an alternative execution of the pleated portion of FIG. 3.

DETAILED DESCRIPTION

Figure 1:
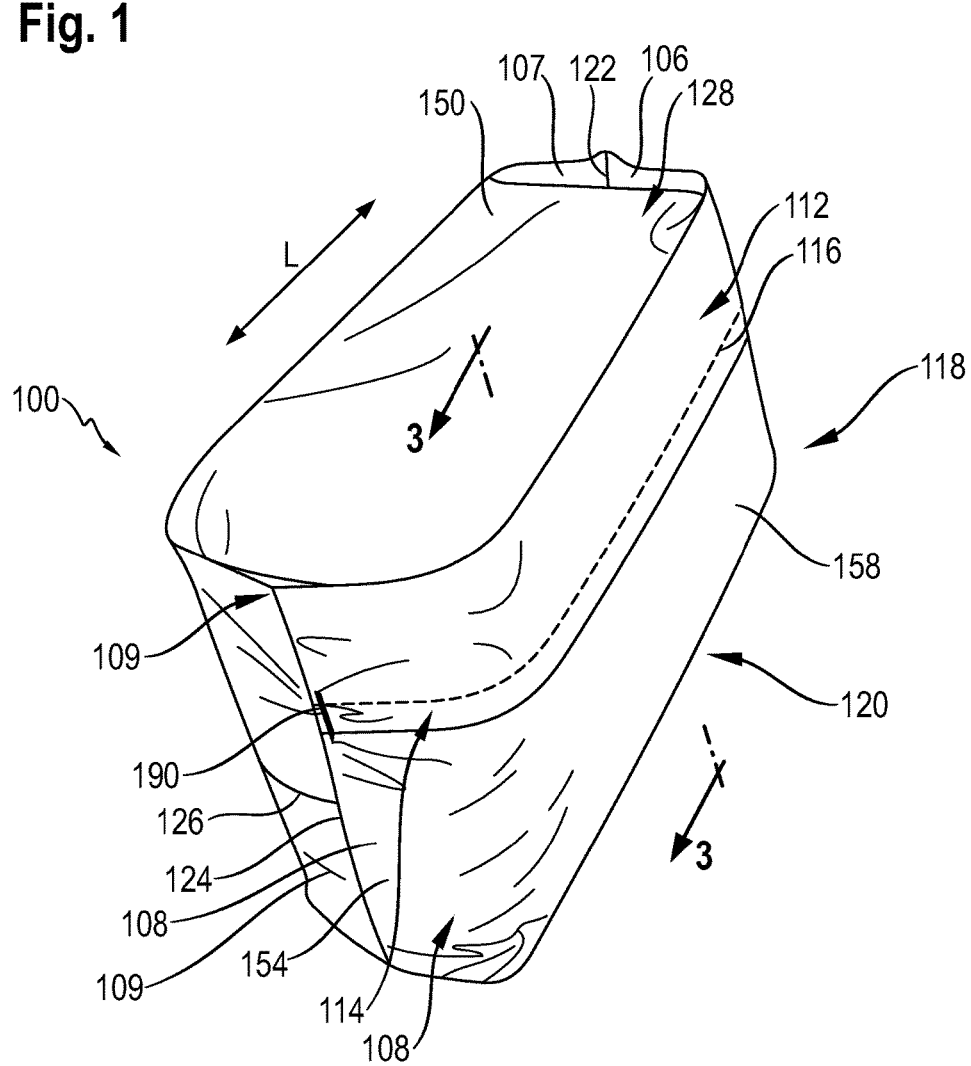
FIG. 1 is a front, perspective view of a sealed, reclosable package.

The following definitions may be useful in understanding the present disclosure.

As used herein, "absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants (for babies or for adults), absorbent inserts (which are intended to be inserted into an outer cover to form a diaper or pant), feminine care absorbent articles such as sanitary napkins or pantiliners, and the like. As used herein, the term "exudates" includes, but is not limited to, urine, blood, vaginal discharges, sweat and fecal matter. Preferred absorbent articles of the present invention are disposable absorbent articles, more preferably disposable diapers and disposable pants.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use.

As used herein, "disposable and compressed consumer products" are products which are made of, or which comprise substantial amounts of compressible components, such as tissues, nonwovens, foams, wadding or the like. Such products are typically packaged and put on sale in a compressed form to reduce the amount of storage and shelf space. Disposable and compressible consumer products also encompass disposable absorbent articles.

As used herein, "diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be preformed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

As used herein, a "pantiliner" and a "sanitary napkin" generally have two end regions and a middle region (i.e. a crotch region). The pantiliner and the sanitary napkin have a body-facing surface and a garment facing surface. The size and shape of the absorbent structure positioned between the topsheet and the backsheet can be altered to meet absorbent capacity requirements, and to provide comfort to the wearer. The garment facing surface of the pantiliner and of the sanitary napkin can have thereon pressure sensitive adhesive for affixing to a wearer's undergarments. Typically, such adhesive is covered with a release strip which is removed before affixing to the undergarment. Pantiliners can also be provided with lateral extensions known commonly in the art as "flaps" or "wings" intended to extend over and cover the panty elastics in the crotch region of the user's undergarment. However, wings are normally not used with pantiliners but are more often used in sanitary napkins. Sanitary napkins and pantiliners of the present invention comprise barrier leg cuffs.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article.

"Lateral" refers to a direction running from a longitudinally extending side edge to a laterally opposing longitudinally extending side edge of an article and generally at a right angle to the longitudinal direction.

"Machine direction" (MD) is used herein to refer to the direction of material flow through a process. In addition, relative placement and movement of material can be described as flowing in the machine direction through a process from upstream in the process to downstream in the process. "Cross-machine direction" (CD) is used herein to refer to a direction that is not parallel with, and usually perpendicular to, the machine direction.

"Sealed" refers herein to a package having an interior that is inaccessible until the package is ruptured.

A first line of weakness being provided "substantially" in the second fold refers herein to a line of weakness which may deviate slightly from the position of the second fold due to manufacturing variations which may be inevitable in a high speed manufacturing process. Such deviations will be unsubstantial and unintended.

The present disclosure relates to flexible, reclosable packages containing disposable compressed consumer products, such as absorbent articles, and further relates to methods of making the same.

The flexible reclosable package is integrally formed from a single piece of material. It has a hexahedral shape with a top panel, a bottom panel, a front panel, a back panel, a left side panel and a right side panel.

The right side panel comprises a first right side panel portion adjacent to the front panel and a second right side panel portion adjacent to the back panel. The first and second right side panel portions are joined to each other along first side panel seam.

The left side panel comprises a first left side panel portion adjacent to the front panel (158) and a second left side panel portion adjacent to the back panel. The first and second left side panel portions being joined to each other along a second side panel seam.

The package has a longitudinal dimension extending from the first side panel seam to the second side panel seam. A third seam joins extends along the longitudinal dimension of the package.

A hooded portion defines the top panel, a portion of the front panel, a portion of the first right side panel portion and a portion of the first left side panel portion.

A pleated portion is provided adjacent to the hooded portion and extends along the longitudinal dimension of the package from the first side panel seam to the second side panel seam through the first right side panel portion, the front panel, and the first left side panel portion, wherein a first line of weakness is provided in the pleated portion.

The flexible reclosable package can be converted from a closed configuration to an open configuration upon opening the package along the line of weakness. The first line of weakness is not visible from the exterior of the package when the package is in the closed configuration.

In the open configuration, the hooded portion and a part of the pleated portion are folded away from the remaining part of the pleated portion to provide access to the interior of the package. Disposable and compressed consumer products, are, for example, absorbent articles and may include diapers, pants, pantiliners, sanitary napkins or absorbent inserts.

By not having the line of weakness being visible from the exterior of the flexible reclosable package when the package is in the first, closed configuration, the risk of inadvertent tearing open the line of weakness is reduced compared to a first line of weakness which is visible—and more easily accessible—from the exterior of the package. Also, the package provides a more aesthetic appearance, as visible first line of weakness may deteriorate the attractiveness of the flexible reclosable package.

Figure 2:
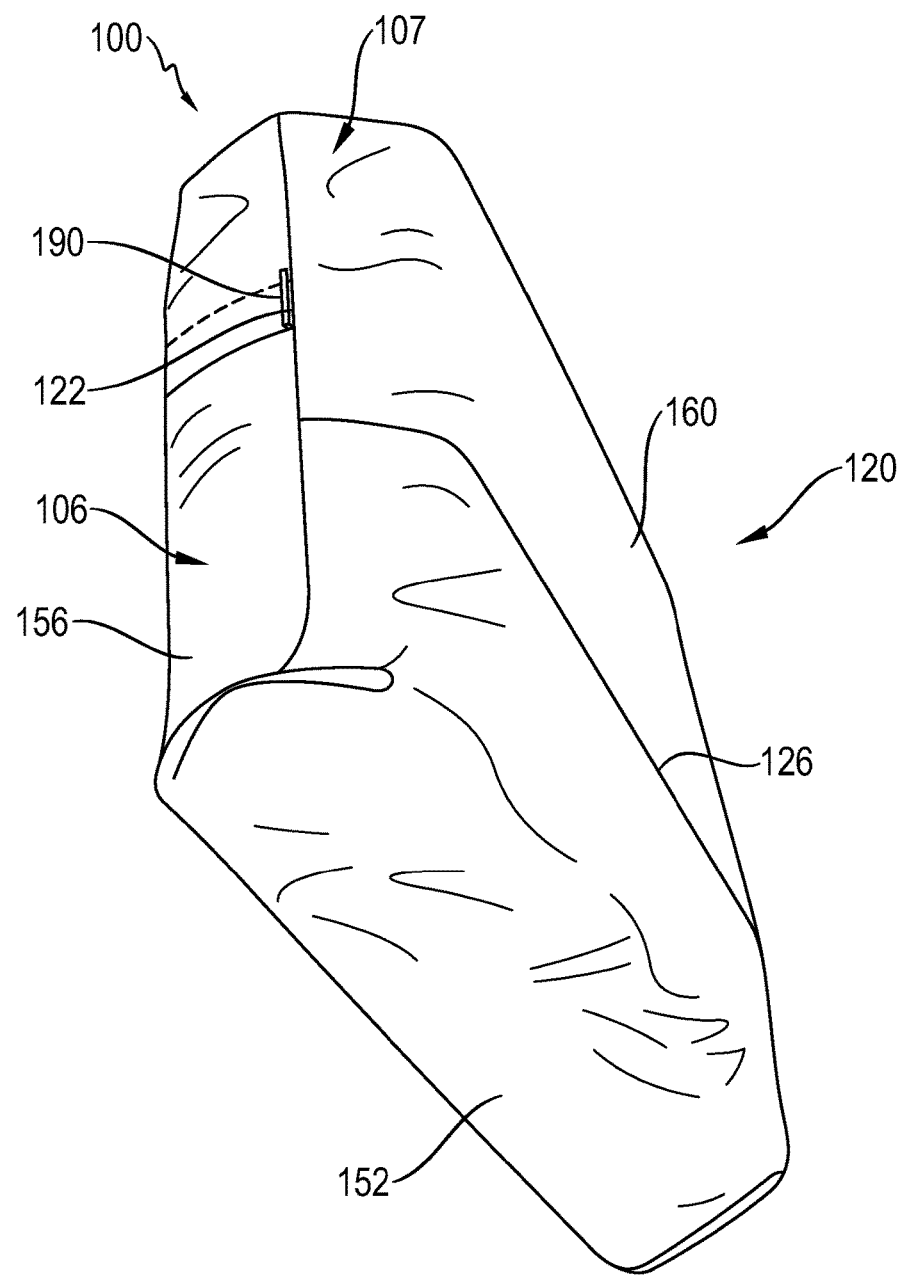
FIG. 2 is a back, perspective view of a sealed, reclosable package.

FIGS. 1-3 illustrate an exemplary package 100 for containing absorbent articles. The first line of weakness is not visible from the exterior of the flexible reclosable package 100 when the package is in the closed configuration (to generally indicate the position of the first line of weakness, FIGS. 1 and 2, 4A, 4B and 6 show the first line of weakness in dotted lines from the exterior of the package. This first line of weakness is however not visible and is thus shown in dotted lines both to emphasize that the line is not visible but is concealed within the pleated portion 114 and to illustrate that the line may not be continuous but may be a discontinuous perforation). The first line of weakness 116 may extend within the pleated portion 114 through the first right side panel portion 106 of the right side panel 156, the front panel 158 and the first left side panel portion 108. The first line of weakness 116 may not extend from the first side panel seam 122 to the second side panel seam 124 but may not extend through and across the first and second side panel seams 122 and 124.

The first and second side panel seams 122 and 124 may be formed in various ways known in the art, such as heat bonding, ultrasonic bonding, pressure bonding, heat and pressure bonding, adhesive bonding or combinations thereof.

The third seam 126 may also be formed in various ways known in the art, such as heat bonding, ultrasonic bonding, pressure bonding, heat and pressure bonding, adhesive bonding or combinations thereof.

Figure 4A:
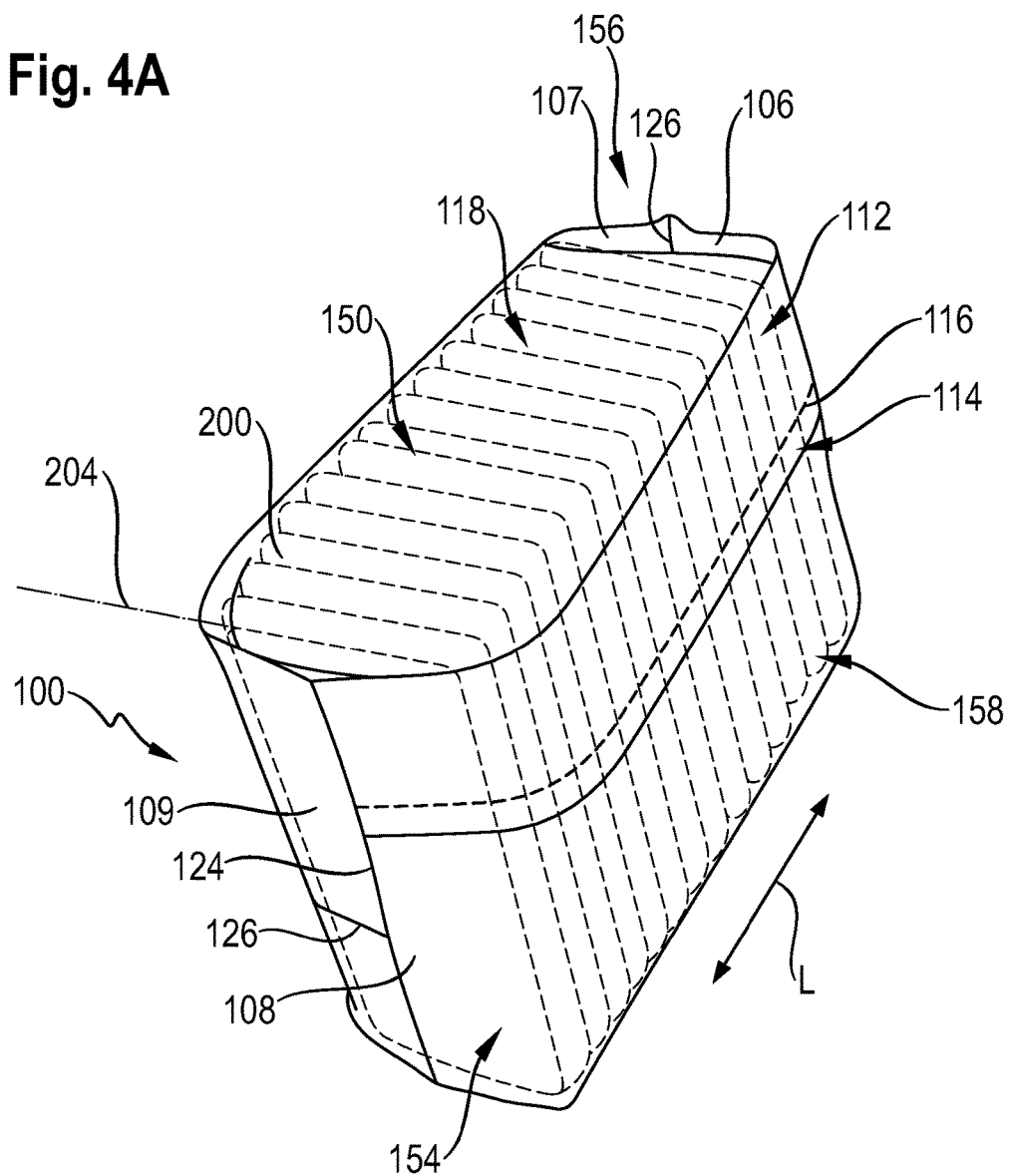
FIG. 4A is a front, perspective view of a sealed, reclosable package having a plurality of absorbent articles contained therein.
Figure 4B:
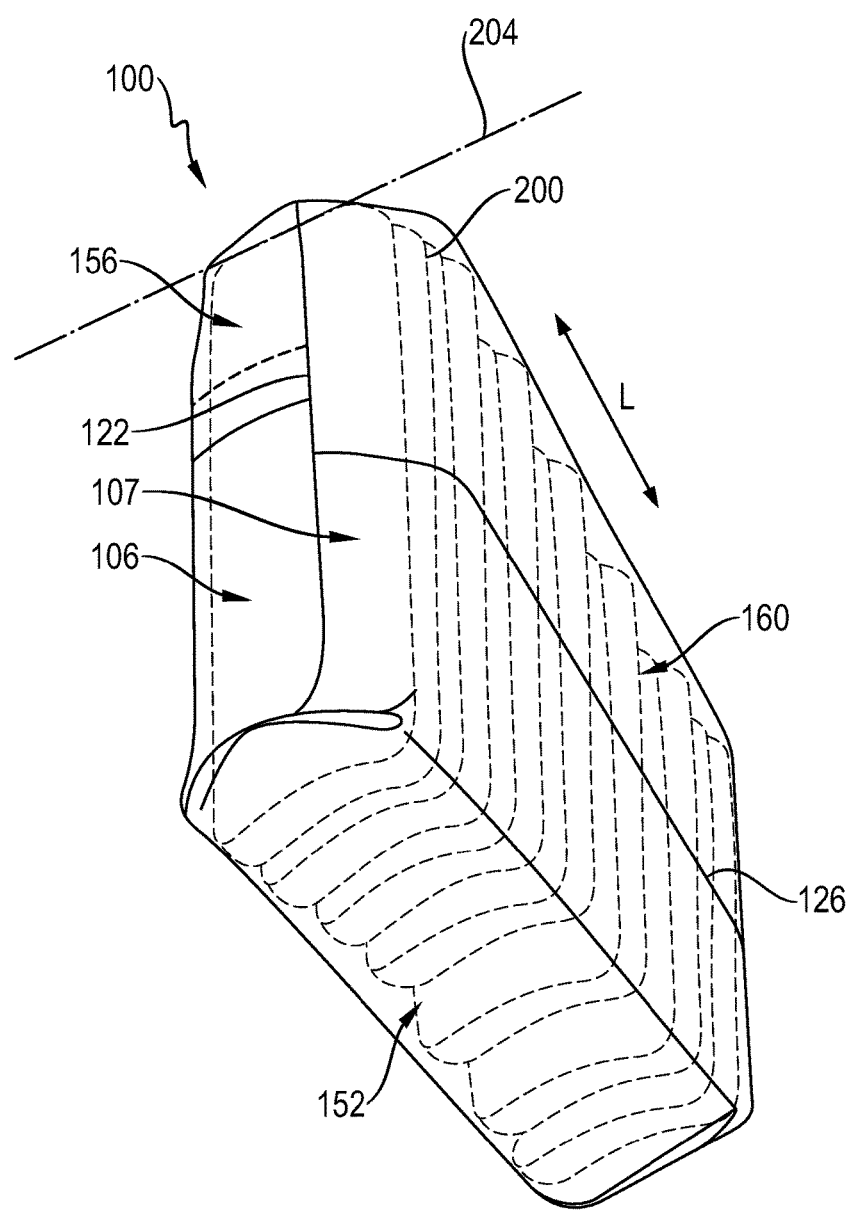
FIG. 4B is a back, perspective view of a sealed, reclosable package having a plurality of absorbent articles contained therein.

As shown in FIGS. 4A and 4B, the disposable and compressed consumer products contained in the package 100 may be a plurality of absorbent articles 200. Each absorbent article 200 may be folded about a lateral axis 204. Each absorbent article may, alternatively, be folded two times about fold lines substantially parallel to the lateral axis of the absorbent article. In such configurations, the folded absorbent article has two fold lines. Still further alternatively, each absorbent article may be folded three times about fold lines substantially parallel to the lateral axis of the absorbent article. In such configurations, the folded absorbent article has three fold lines. The absorbent articles may be arranged in rows with one of the two major, outwardly facing surfaces of the absorbent article contacting a major, outwardly facing surface of the adjacent absorbent articles on one side of the row and the other major, outwardly facing surface of the absorbent article contacts a major, outwardly facing surface of the adjacent absorbent article on the opposite side of the row (as is, for example, shown in FIG. 4A). The term "outwardly facing", as used herein in conjunction with an absorbent article is not to be understood as facing outwardly of the package but is to be understood as not being concealed within the folded absorbent article. Wrapping the continuous length of material 210 around a group of absorbent articles, such as one or more rows of absorbent articles 200, results in formation of a substantially hexahedral shaped package having a top panel 150, bottom panel 152, front panel 158, back panel 160, left side panel 154, and right side panel 156. The row or rows of absorbent articles may extend along the longitudinal dimension L of the package 100. The absorbent articles 200 are compressed to accommodate a relatively large number of articles within the flexible package. At the same time, compressed products, such as compressed absorbent articles provide stability to the flexible package filled with the absorbent articles. Improved stability of the package supports stackability of the packages, for example when they are stacked on a pallet for transport or storage.

As exemplarily shown in FIGS. 4a and 4B, the absorbent articles 200 comprised by the interior of the flexible package 100 may be arranged such that their major, outwardly facing surfaces are facing towards the left and right side panels 154 and 156, respectively, of the flexible package. In such configurations, the absorbent article at the beginning of a row will lie against the left side panel 154 and the absorbent article at the end of a row will lie against the right side panel 156 of the flexible package (they may either directly contact the left and right side panel 154, 156 or a sheet, such as a cardboard or paper may be provided between the respective major surface of the absorbent article and the left and right side panel 154, 156 to provide further stability to the flexible package).

If the absorbent articles are provided in the flexible reclosable package in this manner, repeated opening and closing of the package can be done more easily compared to a package wherein the major, outwardly facing surfaces of the absorbent articles face towards the front and back panel 158, 160 or towards the top and bottom panel 150, 152 of the flexible reclosable package. The hooded portion and a portion of the pleated portion 114 can be easily folded back over the slim, folded edges of the absorbent articles. As more and more absorbent articles are removed from the package, the rows of absorbent articles will start to slant sidewards and the articles in a row are arranged more loosely. If the rows of absorbent articles are arranges such that the major, outwardly facing surfaces of the absorbent articles face towards the front and back panel 158, 160, the slanted absorbent articles may slant towards the front panel 158 and "lean" out of the opened package, which makes reclosing of the package more difficult.

A flexible package may comprise (only) one row of absorbent articles (as, e.g., shown in FIGS. 4A and 4B). Alternatively, a flexible package may comprise more than one row of absorbent articles. In flexible reclosable packages with more than one row of absorbent articles, the rows may either be stacked one on top of the other (leading to a flexible reclosable package with higher front and back panel 158, 160 and higher left and right side panels 154, 156 compared to a package with one row), or, the rows may be provided adjacent to each other (leading to a flexible package with wider left and right side panels 154, 156). In a flexible reclosable package with at least four rows of absorbent articles, the rows may be arranged such that some rows are stacked one of top of the other and other rows are provided adjacent to each other.

With reference to FIGS. 1, 2, 4A, and 4B, the package 100 may be configured such that the bottom panel 152 is intended to be supported by a surface such as a table, countertop, floor, changing table, and the like. However, it is to be appreciated that the package 100 may be configured to rest on any of the top panel 150, bottom panel 152, front panel 158, back panel 160, left side panel 154, or right side panel 156.

With reference to FIG. 1, prior to opening the package 100 at the first line of weakness 116, the package 100 may be sealed. Thus, the package 100 can be prevented from tampering or contamination until the consumer opens the package 100 to remove the first absorbent article. That is, during shipping, storage, and while at the store, the package 100 may remain sealed. As discussed in more detail below, upon opening the package 100 at the first line of weakness 116, the hooded portion 112 and a portion of the pleated portion 114 may be configured from a first, closed configuration to a second, open configuration and back to the first, closed configuration in order to prevent contamination in between uses.

Figure 5:
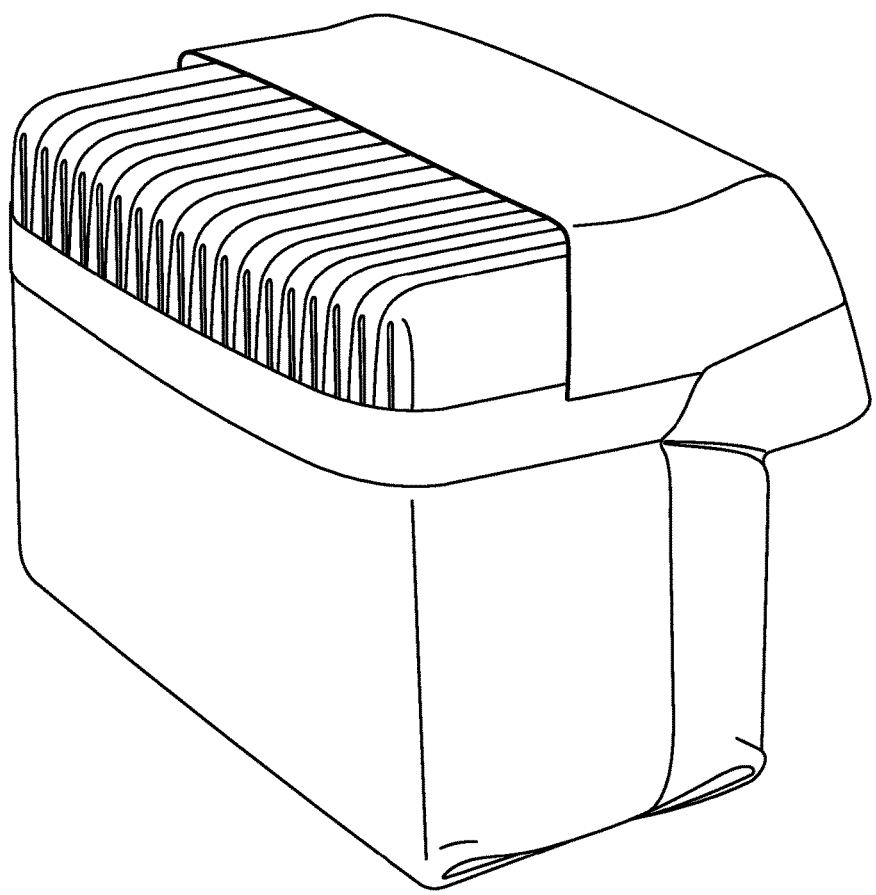
FIG. 5 is a perspective views of a reclosable package with a hooded portion in the second, open configuration.

As shown in FIGS. 1 and 3, the hooded portion 112 defines the top panel 150, a portion of the front panel 158, and a portion of the first left and right side panel portions 106 and 108. The pleated portion 114 is provided adjacent to the hooded portion and extends long the longitudinal dimension L of the package from the first side panel seam 122 to the second side panel seam 124. Upon opening the package 100 along the first line of weakness 116, the hooded portion 112 and a portion of the pleated portion 114 may be arranged in a first configuration and a second configuration. As shown in FIG. 1, in the first configuration, the package 100 is substantially closed such that the hooded portion 112 is positioned adjacent to lower portion of the front panel 158. As shown in FIG. 5, in the second configuration, the hooded portion 112 and a portion of the pleated portion 114 are located away from the lower portion of the front panel 158 and the remaining part of the pleated portion 114 such that a first opening 142 is formed in the package 100. The hooded portion 112 and a portion of the pleated portion 114 may be opened in various degrees to expose different amounts of the absorbent articles 200 contained within the package 100. FIG. 5 shows the flexible package in the second, open configuration.

As shown in FIGS. 3, 3A and 3B, the pleated portion 114 may comprise first and second folds 162 and 164 that form first, second, and third layers 166, 168, and 170, respectively.

The first layer 166 is arranged proximate to the exterior 120 of the package 100 and the second layer 168 is arranged proximate to the interior 118 of the package 100. The third layer 170 separates the first and second layers 166 and 168. The first and third layers 166 and 170 converge at the first fold 162, i.e. the first fold 162 is between the first and the third layer 166 and 170; and the second and third layers 168 and 170 converge at the second fold 164, i.e. the second fold 164 is between the second and the third layer 168 and 170. The first, second and third layers may be configured in a Z-shape. The package 100, including the first and second panels 102 and 104, are integrally formed from a single piece of material.

In flexible reclosable packages 100 wherein the pleated portion 114 has s first, second and third layer 166, 168, and 170, the line of weakness 116 may be provided in the second layer 168 or, more desirably, in the third layer 170. Alternatively, the line of weakness 116 may also be provided substantially in the second fold 164. That way, the line of weakness 116 is not visible from the exterior 120 of the package 100 when the package is in its closed configuration. Thereby, the risk of inadvertent tearing open the line of weakness is reduced compared to a first line of weakness which is visible—and more easily accessible—from the exterior of the package. Also, the package provides a more aesthetic appearance, as visible first line of weakness may deteriorate the attractiveness of the flexible reclosable package.

As the package 100 is torn open along the first line of weakness 116 and the hooded portion 112 and a portion of the pleated portion 114 are pulled open and positioned away from the from the remaining part of the front panel 158 including the remaining part of the pleated portion 114, the portion of the pleated portion 114 which is pulled open with the hooded portion 112 comprises the first layer 166 of the pleated portion and the first fold 162. If the first line of weakness 116 is provided in the third layer 170, the portion of the pleated portion 114 which is pulled open further comprises those parts of the third layer 170 which extend between the first fold 162 and the first line of weakness 116. If the first line of weakness 116 is provided substantially in the second fold 164, the portion of the pleated portion 114 which is pulled open further comprises the complete third layer 170; and if the first line of weakness 116 is provided in the second layer 168, the portion of the pleated portion 114 which is pulled open also comprises the second fold 164 and the portion of the second layer 164 which extends between the second fold 164 and the first line of weakness 116.

Hence, in all these embodiments, i.e. for all possible locations of the first line of weakness 116 encompassed by the present invention, the edge of pleated portion which is pulled away from the remaining part of the pleated portion comprises two layers (the first layer 166 and at least parts of the third layer 170) and the first fold 162. The first fold provides a relatively smooth and stable edge to be pulled back over the disposable consumer products, such as disposable absorbent articles to reclose the package. Also, the two layers (the first layer 166 and parts of the third layer 170) further improve the stability of the edge which is pulled back to reclose the package.

Compared thereto, a package wherein the part of the package, which is pulled away to form an opening, has an edge that is formed by a line of weakness, may be more difficult to reclose: Once the package is open, the (former) line of weakness provides a relatively rough and unstable edge. This edge may often be frayed, which makes it more difficult to pull it back over the disposable consumer products, such as disposable absorbent articles, to reclose the package 100. Also, as the edge is only formed of a single layer, the edge is more flimsy and reclosing the package 100 may be further hindered.

In flexible reclosable packages 100 wherein the pleated portion 114 has a first, second and third layer 166, 168, and 170, the layers may be attached to each other in one or more attachment areas. E.g., the third layer 170 may be attached to the first layer 166 in the area adjacent to the first fold 162 in a first attachment area 195 (shown in FIG. 3B). The first attachment area 195 may be substantially parallel to the first fold 162. The first attachment area 195 may be continuous along the pleated portion 114 from the first right side panel portion 106 to the first left side panel portion 108, or may be discontinuous. The first attachment area may be facilitated by any suitable means known in the art, such as adhesively (e.g. by hot melt adhesive or by pressure sensitive adhesive), by ultrasonic welding, thermo-bonding, pressure-bonding, or combinations thereof. The attachment may be permanent, i.e. not releasable.

In flexible reclosable packages 100 wherein the pleated portion 114 has a first, second and third layer 166, 168, and 170, the third layer 170 may be attached to the second layer 168 in the area adjacent to the second fold 164 by a second attachment area 196 (exemplified in FIG. 3B). The second attachment area 196 may be substantially parallel to the second fold 164. The second attachment area 196 may be continuous along the pleated portion 114 from the first right side panel portion 106 to the first left side panel portion 108, or may be discontinuous. The second attachment area may be facilitated by any suitable means known in the art, such as adhesively (e.g. by hot melt adhesive or pressure sensitive adhesive), by ultrasonic welding, thermo-bonding, pressure-bonding, or combinations thereof.

The attachment in the first and/or second attachment area 195 and 196 may be permanent, i.e. not releasable.

The first and the second attachment area 195 and 196 help to ensure that the first and second fold 162 and 164 remain intact i.e. do not unfold upon breaking open the line of weakness and converting the package from the closed configuration into the open configuration (except, of course, for flexible reclosable packages wherein the first line of weakness is provided substantially in the second fold 164, in which case the second fold 164 disappears upon tearing open the first line of weakness). This not only provides a good aesthetic appearance of the package in its open configuration but also eases the conversion of the package to the open configuration.

Moreover, if the first line of weakness extends through the third layer 170, as the first and second fold 162 and 164 remain intact upon opening the package, and the third layer is separated apart into two portions along the (broken up) first line of weakness, the edges on both sides of the (broken up) first line of weakness 116 in the third layer 170 can engage and interlock with each other when reclosing the package. Hence, reclosing the package and keeping the package reliably in its re-closed configuration can be improved by implementing a first and second attachment area 195 and 196.

On the other side, if the first line of weakness is provided along the second fold 164, the package, in its opened configuration, does not display any surfaces from its interior. That is to say, if the first line of weakness 116 extends through the third layer 170, the portion of the third layer 170 which remains adjacent to the second fold 164 in the opened configuration of the package will be visible with its interior surface folded over to the outside. As the interior surface of the material forming the flexible reclosable package will normally not be printed or otherwise decorated (but will normally be plain white or transparent), the non-decorated inside of the portion of the third layer 170 which is folded over will be facing outwardly and may disturb and interrupt the overall decorated package. Furthermore, from a manufacturing standpoint, folding over the material of the flexible reclosable package in the second fold may be easier after the line of weakness has been provided to be substantially in the second fold.

The pleated portion may have a third attachment area (not shown) in addition to or instead of the first and/or second attachment area(s): The third layer 170 of the pleated portion 114 may be releasably attached to the second layer 168 between the first line of weakness 116 and the first fold 162 in a third attachment area. The third attachment area may be adjacent to the first fold 162. This releasable third attachment area can help to maintain an intimate contact between pleated portion 114 and the first panel 102 prior to tearing open the package along the first line of weakness 116. The releasable third attachment may further be reclosable (i.e. re-attachable, e.g. by use of a suitable pressure sensitive adhesive) such as maintain the reclosed flexible package in (re-)sealed configuration after the package has been opened and reclosed.

Instead of, or in addition to a first, second and/or third attachment areas, the flexible package 100 may comprise distinct materials (not shown) which are joined to the flexible reclosable package for stabilizing of the pleated portion 114, such as adhesive tapes (double or single sided), strings, or the like. Such additional, distinct materials can increase the stiffness, and/or add elasticity and stabilize the configuration of first, second and third layers 166, 168 and 170. For instance, a double sided adhesive tape may be applied continuously within the pleated portion 114, to stabilize. Alternatively, a strip of a thermoplastic material may be applied in the same position and welded, for instance with hot air, ultrasonic welding or other means known in the art.

With reference to FIG. 3, the hooded portion 112 and the pleated portion 114 together define a width, $W_H$, and the remaining part of the front panel 158 below the pleated portion 114 defines a width, $W_{FP}$, of the package 100. The pleated portion 114 has a width $W_P$. The width $W_H$, $W_{FP}$, and $W_P$ are perpendicular to the longitudinal dimension L of the package.

In some exemplary configurations, the width $W_H$ of the hooded portion 112 and pleated portion 114 may be less than the width $W_{FP}$, of the remaining front panel 158. Or, in other exemplary configurations, the width $W_H$ of the hooded portion 112 and pleated portion 114 may be greater than the width, $W_{FP}$, of the remaining front panel 158. Generally, suitable dimensions of $W_H$ and $W_{FP}$ depend, inter alia, on the dimensions of the absorbent articles contained within the package. For diapers or pants, especially for diapers and pants intended to be worn by babies and toddlers, suitable dimensions for $W_H$ may be from 20 mm to 80 mm, or from 30 mm to 70 mm, such as, e.g. about 50 mm, and suitable dimensions for $W_P$ may be from 5 mm to 50 mm, or from 5 mm to 30 mm, such as, e.g. about 20 mm. The dimension is generally not critical for the present invention and will depend, inter alia, on the size of the absorbent articles and on the number of rows of absorbent articles stacked on top of each other within the flexible package.

As shown in FIGS. 1-3, the first line of weakness 116 may extend from the first right side panel portion 106 to the first left side panel portion 108. The first line of weakness 116 may not extend through the first and second side panel seam 122, 124. Thereby, the line of weakness can be stabilized at its starting and end points by the first and second side panel seam 122, 124, helping to reduce the risk of continued tearing and inadvertent opening of the package beyond the starting and end point of the first line of weakness 116. As shown in FIG. 1, the first line of weakness 116 may be substantially linear. However, the first line of weakness 116 may, alternatively be curved, or may be configured in various other shapes.

The first line of weakness 116 may be ruptured by a user to gain access to the interior 118 of the package 100. The first line of weakness 116 shown in FIG. 1 is configured with perforations. However, the first line of weakness 116 may comprise perforations, crimps, or other means to weaken the material that provide a line that is weaker in structure as compared to the portions of package 100 adjacent to the first line of weakness 116.

The first line of weakness 116 may extend completely through the thickness of the flexible material 170 (however, while not being facilitated as a continuous cut but as intermitted, discontinuous small cuts through the material). Alternatively, the first line of weakness may be provided by weakening the material throughout its caliper without fully cutting through the material. For example one or both surfaces of the material may be weakened or eliminated in the areas of the first line of weakness in a continuous or discontinuous manner.

It is to be appreciated that the first line of weakness 116 may be strong enough to withstand shipping and handling of the package 100 without rupture, while being weak enough for a consumer to rupture the first line of weakness 116 at the time of first use of the package 100.

With reference to FIG. 1, the hooded portion 112 may comprise one or more gussets 128. The one or more gussets 128 may be formed by the method described herein for forming the package 100 containing disposable and compressed consumer products after the method step of joining the first and second side edges 217 and 219 to each other to form the third seam 129 along machine direction MD. The gussets may be formed prior to or during sealing the length of continuous material 210 adjacent to the leading edge and the trailing edge of the plurality of disposable and compressed consumer products, such as absorbent articles, to form the first and second side panel seams along cross-machine direction CD. The gussets will then be formed in the left and right side panels 154 and 156.

The first side panel seam 122, which joins the first and second right side panel portion 106 and 107, may not include the first and third layer 166 and 170 of the pleated portion 114. Likewise, the second side panel seam 124, which joins the first and second left side panel portion 108 and 109 may not include the first and third layer 166 and 170 of the pleated portion 114.

Alternatively or in addition to not including the first and third layer 166 and 170 of the pleated portion in the first and second side panel seams 122 and 124, the flexible reclosable package 100 may comprise a slit or a second line of weakness 190 in the pleated portion 114 adjacent to each of the first and second side panel seams 122 and 124 (exemplarily illustrated in FIGS. 1 and 2). The slit or second line of weakness 190 extends along the first and second side panel seam, respectively. Hence, the slit or second line of weakness 190 extends through the pleated portion 114 towards the hooded portion 112. If the pleated portion 114 has s first, second and third layer 166, 168, and 170, the slit or second line of weakness 190 extends from the first fold 162 through the first and third layer 166 and 170. The slit or second line of weakness 190 may not extend through the second layer 168 to avoid the creation of an opening in the package while the package is in its closed configuration. Such an opening may allow dust or other small items to unintentionally enter the interior 118 of the package 100.

The slit or second line of weakness 190 may not extend into the hooded portion—for the same reasons as the slit of second line of weakness may not extend through the second layer 168 of the pleated portion 114 (i.e. the creation of the opening in the package).

However, if a second line of weakness 190 is applied instead of a slit 190, the second line of weakness 190 may, alternatively, extend through the second layer 168 of the pleated portion 114, as the second line of weakness 190 will only be opened in conjunction with opening the first line of weakness 116. Hence, while the flexible reclosable package 100 is stored, transported or presented on the shelf in a store, the flexible reclosable package 100 has no opening.

By providing a slit or second line of weakness 190, and/or by not including the first and third layer 166 and 170 of the pleated portion 114 in the first and second side panel seam 122 and 124, opening and reclosing the flexible reclosable package can be improved. The hooded portion 112 and portion of the pleated portion 114 can slide upwards and downwards more easily and smoothly, as the strain applied to the hooded portion and portion of the pleated portion 114 along the first right side panel portion 106 to the first left side panel portion 108 (across the package in the hooded portion along the longitudinal dimension L) is reduced. Ease of up- and down-sliding can be especially improved when the package is filled with compressed absorbent articles, and no (or only very few) articles have yet been removed from the package. Without providing the slit or second line of weakness 190 along the first and second side panel seam 122 and 124, a user may find it difficult to open and reclose the package by lifting the hooded portion 112 and portion of the pleated portion 114. Moreover, by forcing the package to open, the portion of the pleated portion and the hooded portion may tear at random locations to relieve the strain applied to the hooded portion and portion of the pleated portion 114 along the first right side panel portion 106 to the first left side panel portion 108.

With reference to FIGS. 1 and 2, the packages 100 may comprise or consist of various flexible materials. For example, the packages 100 may comprise or consist of films made from materials such as polyolefins, for example polyethylene or polypropylene. The flexible package 100 may comprise or consist of a polyethylene-polypropylene-polyethylene laminate. The package may be made of a LDPE (low density polyethylene) mono-layer film or may be made of a film of co-extruded LDPE and HDPE (high density polyethylene) layers. The flexible reclosable package may also comprise or consist of a film of polypropylene, such as, for example, high density polypropylene and/or low density polypropylene. If the package 100 comprises a laminate, the laminate may be co-extruded. The material of the flexible reclosable package 100 may have a thickness from about 35 μm to about 150 μm, or from about 40 μm to about 120 μm, or from about 40 μm to about 100 μm.

In some exemplary configurations, components of the package can at least partially be comprised of bio-sourced content such as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011.

The flexible package may comprise a bio-based content value from 10% to 100%, or from 25% to 75%, or from 50% to 60%, using ASTM D6866-10, method B.

In order to apply the methodology of ASTM D6866-10 to determine the bio-based content of any package, a representative sample of the package must be obtained for testing. In at least one exemplary configuration, the package can be ground into particulates less than about 20 mesh using known grinding methods (e.g., Wiley® mill), and a representative sample of suitable mass taken from the randomly mixed particles.

The flexible package 100 may additionally comprise one or more fastening stripes, such as tapes, which extend from and bridge the pleated portion 114 to the front panel 158 adjacent to the pleated portion 114. The one or more fastening stripes may be permanently attached to the package in the area of the pleated portion 114 and may be releasably attached to the front panel 158. The one or more fastening stripes may have a grip portion at one end adjacent to the releasable attachment which may ease opening of the package by lifting the fastening stripe(s) to thereby opening the package along the first line of weakness 116. The one or more fastening stripes many also be used to assist keeping the flexible package in its re-closed configuration.

The exterior of the package 100 may comprise various images, colors, text, and the like. The package 100 may have indicia printed on the first and/or second panels 102 and 104, such that when the package 100 is placed with the bottom panel 152 facing down and the top panel 150 facing up, the indicia is oriented so that the indicia appears as upright. Such indicia may include words, e.g. brand name, size, product line, advertising, marketing claims, safety information, instructions for use, and the like, and/or graphics, e.g. pictures of users of the absorbent articles, caregivers, purchasers of the absorbent articles, advertising, and pictorial depictions of safety information and/or instructions for use, and the like.

The first line of weakness 116 is not visible when viewing the exterior 120 of the package when the package is in the closed configuration. Hence, an indicia may be provided at an appropriate position of the exterior package, such as an arrow or "tear here" statement in order to direct the skilled person toward proper opening of the package along the first line of weakness 116.

The hooded portion 112 may comprise different colors or patterns than the remainder of the package 100. For example, in such an exemplary configuration, the hooded portion 112 may be clear while the remainder of the package comprises a color and/or pattern of colors. In addition, the package 100 may comprise indicia that draws attention to the hooded portion 112 of the package 100 and/or demonstrates how to use the hooded portion 112 of the package 100. For example, an image may comprise a hand and a perspective view of the package and may demonstrate the movement of the hand relative to the package required to arrange the hooded portion and a portion of the pleated portion in the first and second configurations.

Figure 6:
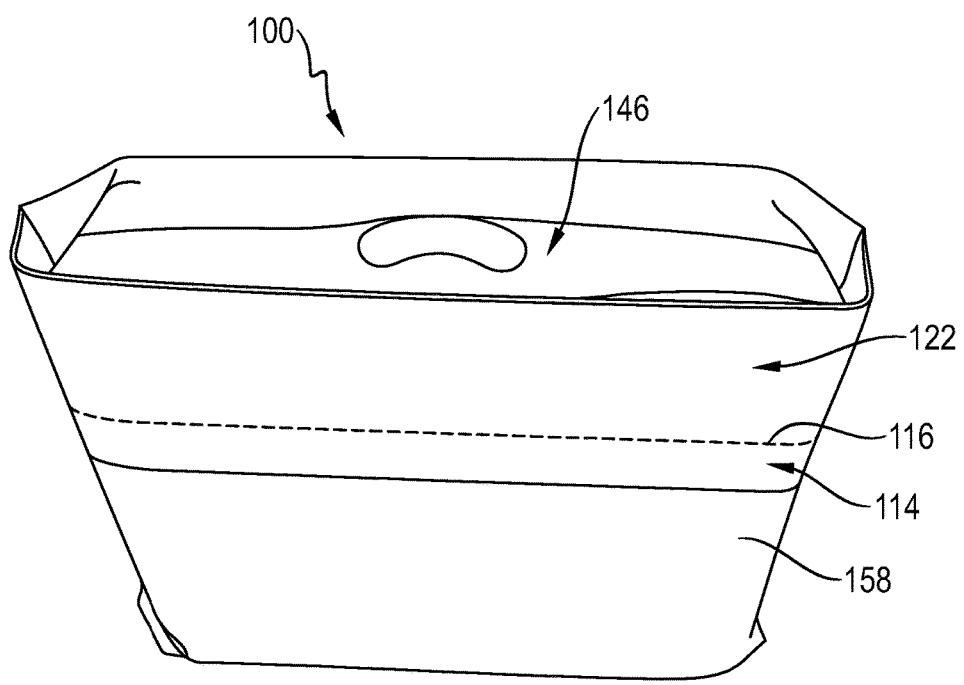
FIG. 6 is a front, perspective view of a sealed, reclosable package having a handle.

As shown in FIG. 6, the package 100 may comprise a handle 146. The handle 146 may be configured in various ways. The handle 146 may be integrally formed from the single piece of material. Alternatively, the handle 146 may be a separate component that is attached to the package 100. The handle 146 may be provided on the top panel 150. The handle may extend along the longitudinal dimension L of the package and may be attached to the package in or adjacent to the first and second side panel seam 122, 124.

With reference to FIGS. 1 and 5, to open the flexible reclosable package 100, a consumer may hold the package 100 below the pleated portion (towards the bottom panel) with fingers from one hand and may hold the hooded portion 112 of the second panel 104 near the pleated portion 114 with fingers from the other hand. The person may rupture the first line of weakness 116 by pulling his or her hands apart in opposite directions until the first line of weakness 116 is fractured. Once the first line of weakness 116 is fractured, the hooded portion 112 and a portion of the pleated portion 114 may be configured from the first, closed configuration to the second, open configuration.

With continuing reference to FIGS. 1 and 5, when a consumer is ready to remove an absorbent article 200 from the package 100, the consumer may configure the hooded portion 112 and a portion of the pleated portion 114 of the package 100 from the first configuration to the second configuration. To configure the hooded portion 112 and a portion of the pleated portion 114 in the second configuration, the consumer may grasp the hooded portion 112 at various locations with one or both hands and simultaneously move the hooded portion 112 and a portion of the pleated portion 114 away from the remaining part of the pleated portion 114 until the absorbent articles 200 are exposed through the first opening 142 in the package 100. At the same time, the user may hold another portion of the package 100 with the opposite hand. Once the user has removed an absorbent article 200 from the package 100, the user may close the hooded portion 112, including the portion 114 of the pleated portion, of the package 100 to protect the absorbent articles 200 from contamination and tampering in between uses. To close the package 100, the hooded portion 112 and the portion of the pleated portion 114 of the package 100 may be positioned back in the first configuration by grasping a portion of the hooded portion 112 with one or both hands and moving the hooded portion 112 over the absorbent articles 200 and toward the pleated portion 114 of the first panel 102. At the same time, the user may hold another portion of the package 100 with the opposite hand. The steps of opening and closing the package 100 by configuring the hooded portion 112 and a portion of the pleated portion 114 in the first and second configurations may be repeated until all of the absorbent articles 200 are removed from the package 100.

Figure 7:
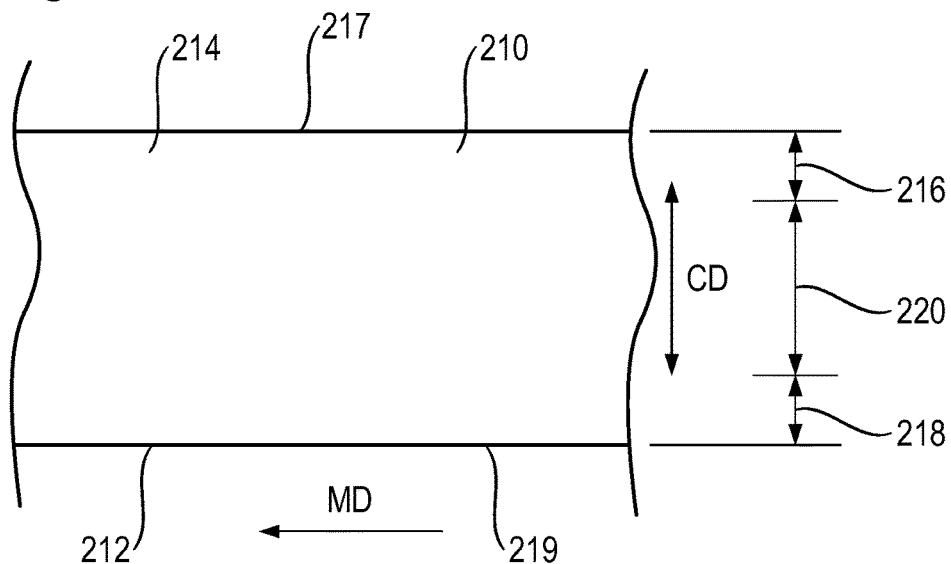
FIG. 7 is a schematic, plan view of a continuous length of material.
Figure 8:
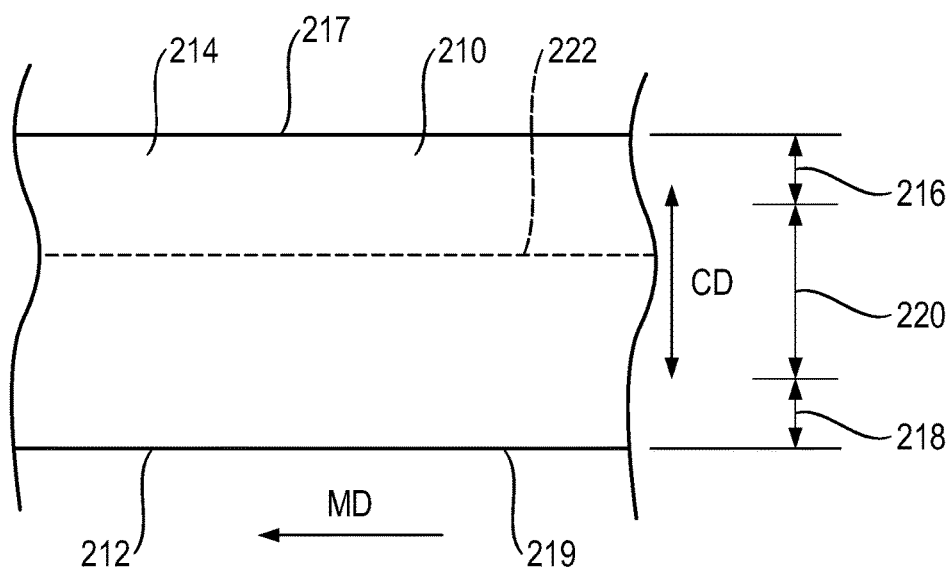
FIG. 8 is a schematic, plan view of a continuous length of material having a continuous first line of weakness.

A method of forming a flexible reclosable package 100, comprises the steps of:

a. Advancing a continuous length of material 210 in a machine direction MD, wherein the continuous length of material 210 has a first side 212 and a second side 214 and defines a first edge region 216 with a first side edge 217 and a second edge region 218 with a second side edge 219 separated in a cross-machine direction CD by a central region 220; see FIG. 7.

b. Forming a line of weakness 222 along the machine direction MD of the central region 220 of the continuous length of material 210; see FIG. 8. Step b. may be done after step a.

c. Folding the continuous length of material along the machine direction MD to form a continuous pleat, wherein the continuous pleat comprises first and second continuous folds that form first, second, and third overlapping continuous pleated portions, wherein the third continuous pleated portion is positioned between the first continuous pleated portion and the second continuous pleated portion, wherein the line of weakness is provided in the continuous pleat, wherein the first and second continuous folds 234 and 236 extend in the machine direction MD. The line of weakness may be provided in the third continuous pleated portion, substantially in the second continuous fold, or, though less desirable, in the second continuous pleated portion. Method step b may be done prior to step c.

d. Advancing a plurality of consumer products, such as disposable absorbent articles, along machine direction MD wherein the plurality of consumer products are arranged in a group, the group having, along machine direction MD, a leading edge and a trailing edge. The leading edge is positioned ahead of the trailing edge when viewed in machine direction. The group of consumer goods may be one or more rows of absorbent articles.

e. Folding the continuous length of material 210 comprising the line of weakness and the pleated portion, around the plurality of consumer products arranged in a group. The third seam may be positioned in the back panel, the bottom panel, the top panel, or even, though less preferred, in the front panel of the flexible reclosable package formed by this method.

f. Joining the first and second side edges 217 and 219 of the continuous length of material 210 to each other to form a continuous third seam 129 along machine direction MD. The continuous third seam forms a continuous tube of the continuous length of material wherein the plurality of consumer products arranged in a group is comprised. The continuous tube may comprise more than one plurality of consumer products arranged in a group (i.e. more than one group). The more than one group may be spaced from each other along machine direction.

g. Sealing the continuous length of material 210 along cross-machine direction CD adjacent to the leading edge and the trailing edge of the plurality of consumer products arranged in a group, thereby forming the first and second side panel seams 122, 124 of the flexible enclosable package and forming a closed package around the plurality of consumer products arranged in a group. Step g. may be done after steps a. to f.

h. Cutting the continuous length of material 210 in the cross-machine direction CD in or adjacent to the first and second side panel seams 122, 124 to form a hexahedral-shaped flexible reclosable package 100 having a front panel 158, a back panel 160, a bottom panel 152, a top panel 150 and left and right side panels 154 and 156. The central region 220 of the continuous length of material 210 forms the front panel 158, the first right side panel portion 106 and the first left side panel portion 108 of the package 100. Step h. may be done after steps a. to g.

In the flexible reclosable package 100 formed by this method, the second continuous pleated portion formed in the continuous length of material 210 will form the second layer 168 of pleated portion 114, which is arranged proximate to the interior 118 of the package. The first continuous pleated portion formed in the continuous length of material 210 will form the first layer 166 of pleated portion 114, which is arranged proximate to the exterior 120 of the package.

The method may further comprise the step of forming a gusset in one or both of the left and right side panels of the flexible reclosable package prior to, after step f.

Several groups of consumer products, such as absorbent articles may be advanced along machine direction (MD) and be subjected to steps d. to g., such that the first and second side panel seams are formed between the groups of consumer products cutting the continuous length of material in step g. simultaneously forms the first side panel seam of one group of consumer products and the second side seam panel of the adjacent group of consumer products.

The plurality of consumer products arranged in a group, such as disposable absorbent articles, may be held in a compressed state prior to folding the continuous length of material around the products.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A flexible reclosable package integrally formed from a single piece of material, the package containing disposable and compressed consumer products, the package having a hexahedral shape with a top panel, a bottom panel, a front panel, a back panel, a left side panel and a right side panel;
    the right side panel comprising a first right side panel portion adjacent to the front panel and a second right side panel portion adjacent to the back panel, the first and second right side panel portions being joined to each other along first side panel seam,
    the left side panel comprising a first left side panel portion adjacent to the front panel and a second left side panel portion adjacent to the back panel, the first and second left side panel portions being joined to each other along a second side panel seam;
    wherein the package has a longitudinal dimension extending from the first side panel seam to the second side panel seam;
    wherein a third seam extends along the longitudinal dimension of the package;
    wherein a hooded portion defines the top panel, a portion of the front panel, a portion of the first right side panel portion and a portion of the first left side panel portion;
    wherein a pleated portion is provided adjacent to the hooded portion and extends along the longitudinal dimension of the package from the first side panel seam to the second side panel seam through the first right side panel portion, the front panel, and the first left side panel portion, wherein a first line of weakness is provided in the pleated portion;
    wherein the flexible reclosable package can be converted from a closed configuration to an open configuration upon opening the package along the first line of weakness, and wherein the first line of weakness is not visible from the exterior of the package when the package is in the closed configuration;
    wherein a slit or a second line of weakness is provided in the pleated portion adjacent to each of the first and second side panel seam and extends along the first and second side panel seam, respectively; and
    wherein the slit or second line of weakness extends from the first fold through the first and third layer, but does not extend through the second layer.

2. The flexible reclosable package of claim 1, wherein the package has an interior facing towards the consumer products and an exterior, wherein the pleated portion comprises a first fold and a second fold that form a first layer, a second layer, and a third layer, wherein the first layer is arranged proximate to the exterior of the package and the second layer is arranged proximate to the interior of the package, the first and third layer converging at the first fold and the third and second layer converging at the second fold, and wherein the first line of weakness is provided in the third layer.

3. The flexible reclosable package of claim 2, wherein the first line of weakness is provided substantially in the second fold.

4. The flexible reclosable package of claim 3, wherein the first and second side panel seams do not include the first and third layer of the pleated portion.

5. The flexible reclosable package of claim 2, wherein the third layer is attached to the first layer in a first attachment area adjacent to the first fold.

6. The flexible reclosable package of claim 2, wherein the third layer is attached to the second layer in the second attachment area adjacent to the second fold.

7. The flexible reclosable package of claim 1, wherein the first line of weakness extends from the first side panel seam to the second side panel seam but does not extend through the first and second side panel seam.

8. The flexible reclosable package of claim 1, wherein the third seam is provided in the back panel or in the bottom panel.

9. The flexible reclosable package of claim 1, wherein the disposable compressed consumer products are a plurality of absorbent articles.

10. The flexible reclosable package of claim 9, wherein the absorbent articles are arranged in one or more rows of absorbent articles, wherein the major, outwardly facing surfaces of the absorbent articles are facing towards the left and right side panels, respectively.

11. The flexible reclosable package of claim 1, wherein upon tearing open the package at the first line of weakness, the hooded portion and a portion of the pleated portion can be arranged in a first configuration and a second configuration; and wherein the flexible reclosable package is closed in the first configuration, and wherein the hooded portion and a portion of the pleated portion, in the second configuration, are positioned away from the remaining part of the front panel, including the remaining part of the pleated portion to define an opening in the package.

* * * * *